(12) United States Patent
Singh et al.

(10) Patent No.: US 8,173,671 B2
(45) Date of Patent: *May 8, 2012

(54) TOPICAL OPHTHALMIC OR OTIC SOLUTION FORMULATIONS CONTAINING MOXIFLOXACIN HYDROCHLORIDE AND DEXAMETHASONE PHOSPHATE

(75) Inventors: Onkar N. Singh, Arlington, TX (US); Suresh C. Dixit, Fort Worth, TX (US); Michael Wall, Fort Worth, TX (US)

(73) Assignee: Alcon Research, Ltd., Forth Worth, TX (US)

( * ) Notice: Subject to any disclaimer, the term of this patent is extended or adjusted under 35 U.S.C. 154(b) by 18 days.

This patent is subject to a terminal disclaimer.

(21) Appl. No.: 12/967,250

(22) Filed: Dec. 14, 2010

(65) Prior Publication Data

US 2011/0082125 A1    Apr. 7, 2011

Related U.S. Application Data

(63) Continuation of application No. 12/276,823, filed on Nov. 24, 2008, now Pat. No. 7,888,370.

(60) Provisional application No. 60/990,452, filed on Nov. 27, 2007.

(51) Int. Cl.
*A61K 31/44* (2006.01)
*A61K 31/56* (2006.01)

(52) U.S. Cl. .................. 514/305; 514/171; 514/178
(58) Field of Classification Search .................. 514/171, 514/178, 305
See application file for complete search history.

(56) References Cited

U.S. PATENT DOCUMENTS

| | | | |
|---|---|---|---|
| 2,939,873 A | 6/1960 | Chemerda et al. | |
| 4,990,517 A | 2/1991 | Petersen et al. | |
| 5,387,589 A | 2/1995 | Kulkarni | |
| 5,397,771 A | 3/1995 | Bechgaard et al. | |
| 5,407,926 A | 4/1995 | Clark | |
| 5,607,942 A | 3/1997 | Petersen et al. | |
| 5,679,665 A | 10/1997 | Bergamini et al. | |
| 6,716,830 B2 | 4/2004 | Cagle et al. | |
| 2002/0022629 A1 | 2/2002 | Cagle et al. | |
| 2002/0193370 A1 | 12/2002 | Cagle et al. | |

FOREIGN PATENT DOCUMENTS

WO    WO0189495 A2    11/2001

OTHER PUBLICATIONS

Hebert, III, et al., "Tympanostomy tubes and otic suspensions: Do they reach the middle ear space?" Otolaryngology-Head and Neck Surgery, 2000, pp. 330-333, vol. 122, No. 3.
Kenya Pharmacy & Poisons Board, Registered Drugs, (Online) http://www.pharmacyboardkenya.org/index.php? id=13&an=M&s-APDROP, copyright 2007 Pharmacy & Poisons Board, pp. 1-2, printed from website on Nov. 10, 2010.
Shabbir Medical Hall, Dispensing Chemists & Druggists, (Online) http://www.shabbirmedicalhall.com/ProductDetails. aspx?productID=1490, copyright 2004-2010, p. 1, printed from website on Nov. 10, 2010.
Central Drugs Standard Control Organization, Directorate General of Health Services, Ministry of Health and Family Welfare, Government on India, List of Drugs Approved During 2005 (Online) http://www.cdsco.nic.in/list_of_drugs_approved_2005.htm, printed from website on Nov. 10, 2010.
Order S.O. 2043(E), Published in Part II, Section 3, Sub-section (ii) of the Gazette of India, Extraordinary, dated Nov. 30, 2007, Government of India, Ministry of Chemicals and Fertilizers, National Pharmaceutical Pricing Authority, New Delhi, the 30th day of Nov. 2007, (Online) http://nppaindia.nic.in/ceiling/press30nov07/so2043e-30-11-07.html, pp. 1-2, printed from website on Nov. 10, 2010.

*Primary Examiner* — Zohreh Fay
(74) *Attorney, Agent, or Firm* — Patrick M. Ryan

(57) ABSTRACT

Topical ophthalmic and otic solution compositions of moxifloxacin and dexamethasone phosphate are disclosed.

1 Claim, No Drawings

TOPICAL OPHTHALMIC OR OTIC SOLUTION FORMULATIONS CONTAINING MOXIFLOXACIN HYDROCHLORIDE AND DEXAMETHASONE PHOSPHATE

This application is a continuation application of U.S. Ser. No. 12/276,823, filed Nov. 24, 2008, now U.S. Pat. No. 7,888,370 which claims priority to U.S. Provisional Application, U.S. Ser. No. 60/990,452, filed Nov. 27, 2007.

BACKGROUND OF THE INVENTION

This invention relates to solution formulations of moxifloxacin and dexamethasone phosphate suitable for topical administration to the eye or ear.

Moxifloxacin is a known antibiotic compound. See, for example, U.S. Pat. Nos. 4,990,517 and 5,607,942. A topically administrable ophthalmic solution containing moxifloxacin is commercially available as VIGAMOX® (moxifloxacin HCl ophthalmic solution), 0.5% as base, from Alcon Laboratories, Inc. See U.S. Pat. No. 6,716,830. The '830 patent discloses compositions specifically formulated for topical application to ophthalmic, otic, and nasal tissues. The '830 patent discloses moxifloxacin compositions optionally containing an anti-inflammatory agent. Disclosed anti-inflammatory agents include steroidal and non-steroidal anti-inflammatory agents. According to the '830 patent, the preferred steroidal anti-inflammatory agents for ophthalmic and otic use include dexamethasone, loteprednol, rimexolone, prednisolone, fluorometholone, and hydrocortisone. A suspension composition containing moxifloxacin and dexamethasone (micronized) and having a pH of 5.5 is provided in Example 2 of the '830 patent. The '830 patent does not specifically disclose any solution compositions containing moxifloxacin and dexamethasone phosphate.

Dexamethasone phosphate is a known form of dexamethasone. See, for example, U.S. Pat. No. 2,939,873. This form of dexamethasone has been used in topical ophthalmic and otic compositions. See, for example, U.S. Pat. No. 5,679,665.

What is needed are stable, preserved, multi-dose solution compositions of moxifloxacin and dexamethasone that are suitable for topical administration to the eye and ear.

SUMMARY OF THE INVENTION

The compositions of the present invention are aqueous compositions of moxifloxacin and dexamethasone. The compositions are stable, preserved, multi-dose solution compositions. The compositions, which are topically administrable to the eye or ear, consist essentially of moxifloxacin hydrochloride, dexamethasone phosphate, edetate disodium, an ionic tonicity adjusting agent, boric acid, a nonionic surfactant, and either benzalkonium chloride or sorbitol. The compositions have a pH of 7.5-8.1.

DETAILED DESCRIPTION OF THE INVENTION

Unless indicated otherwise, all ingredient concentrations are presented in units of % weight/volume (% w/v).

Moxifloxacin is preferably present in the compositions of the present invention in the form of a pharmaceutically acceptable salt. Most preferably, moxifloxacin is present in the form of moxifloxacin hydrochloride. The compositions contain moxifloxacin in an amount equivalent to about 0.5% as the free base. The amount of moxifloxacin hydrochloride in the compositions of the present invention is 0.5-0.6%, and is most preferably 0.545%, which is equivalent to 0.5% moxifloxacin as base.

In addition to moxifloxacin, the aqueous compositions of the present invention contain dexamethasone phosphate. Dexamethasone phosphate is the required form of dexamethasone. Other known forms of dexamethasone, such as the 21-alcohol or 21-acetate form, do not permit the composition to be a solution composition. Suspension compositions are not as desirable for topical administration to the eye or ear as solution compositions because suspensions do not penetrate ophthalmic or otic tissues as well as solutions. The compositions of the present invention contain dexamethasone phosphate in an amount of about 0.1-0.12%. Preferably, the compositions of the present invention contain a pharmaceutically acceptable salt of dexamethasone phosphate in an amount equivalent to about 0.1-0.12% dexamethasone phosphate. For example, the compositions of the present invention may contain dexamethasone sodium phosphate in an amount of 0.10-0.132%. Most preferably, the compositions of the present invention contain 0.11% dexamethasone sodium phosphate, which is equivalent to 0.1% dexamethasone phosphate. Preferably, the compositions of the present invention contain dexamethasone in the form of dexamethasone sodium phosphate.

The compositions of the present invention contain boric acid in an amount from 0.2-0.4%, preferably 0.3%.

Edetate disodium is present in the compositions of the present invention in an amount of 0.005-0.02%. Most preferably, the edetate disodium is present in an amount of 0.01%.

An ionic tonicity adjusting agent is added to the compositions of the present invention in an amount sufficient to cause the final composition to have an osmolality of 270-330 mOsm/Kg. Preferably, the ionic tonicity adjusting agent is sodium chloride and is present in an amount of 0.5-0.75%. Most preferably, the compositions of the present invention contain 0.62% NaCl.

The compositions of the present invention contain an otically and ophthalmically acceptable non-ionic surfactant, such as a polysorbate surfactant, a block copolymer of ethylene oxide and propylene oxide surfactant (e.g., a pluronic or tetronic surfactant), or tyloxapol. Preferably, the compositions contain the non-ionic surfactant in an amount of 0.04-0.06%. Most preferably, the non-ionic surfactant is tyloxapol and the amount of tyloxapol in the compositions of the present invention is 0.05%.

The compositions contain a preservative ingredient or a preservation-enhancing ingredient selected from the group consisting of benzalkonium chloride and sorbitol. Preferably, the compositions of the present invention contain benzalkonium chloride if they are intended for topical otic administration and sorbitol if they are intended for topical ophthalmic administration. If present, the amount of benzalkonium chloride in the compositions is 0.005-0.015%, preferably 0.01%. If present, the amount of sorbitol in the compositions of the present invention is 0.1-0.3%, preferably 0.2%.

The pH of the aqueous solutions of the present invention is adjusted with an ophthalmically acceptable pH-adjusting agent. Ophthalmically acceptable pH adjusting agents are known and include, but are not limited to, hydrochloric acid (HCl) and sodium hydroxide (NaOH). The compositions of the present invention preferably contain NaOH or HCl to obtain the desired pH. The compositions of the present invention are formulated and maintained within a narrow pH range in order to keep the compositions stable over a commercially acceptable shelf-life period. The compositions of the present invention have a pH of 7.5-8.1, and most preferably 7.8-8.0.

The compositions of the present invention are preferably packaged in multi-dose plastic containers designed to deliver drops to the eye or ear. Preferably the plastic is low density polyethylene (LDPE) or polypropylene. Most preferably, the plastic is LDPE.

The following examples are intended to illustrate, but not limit, the present invention.

Example 1

Topical Ophthalmic Solution

| Ingredient | Formulation A (% w/v) |
|---|---|
| Moxifloxacin Hydrochloride | 0.5-0.6 |
| Dexamethasone Sodium Phosphate | 0.10-0.12 |
| Edetate Disodium | 0.005-0.02 |
| NaCl | 0.5-0.75 |
| Boric Acid | 0.2-0.4 |
| Sorbitol | 0.1-0.3 |
| Tyloxapol | 0.04-0.06 |
| NaOH/HCl | q.s. pH 7.5-8.1 |
| Purified Water | q.s. 100 |

Example 2

Preferred Topical Ophthalmic Solution

| Ingredient | Formulation B (% w/v) |
|---|---|
| Moxifloxacin Hydrochloride | $0.545^a$ |
| Dexamethasone Sodium Phosphate | $0.11^b$ |
| Edetate Disodium | $0.01^c$ |
| NaCl | 0.62 |
| Boric Acid | 0.3 |
| Sorbitol | 0.2 |
| Tyloxapol | 0.05 |
| $NaOH^d$/HCl | q.s. pH 7.8-8.0 |
| Purified Water | q.s. 100 |

$^a$0.545% is equivalent to 0.5% moxifloxacin as base
$^b$0.11% is equivalent to 0.1% dexamethasone phosphate
$^c$Edetate disodium, dehydrate is used
$^d$Sodium hydroxide equivalent to 0.0972% is added to facilitate dissolution of moxifloxacin hydrochloride. Additional NaOH may be added if required for pH adjustment.

Example 3

Topical Otic Solution

| Ingredient | Formulation C (% w/v) |
|---|---|
| Moxifloxacin Hydrochloride | 0.5-0.6 |
| Dexamethasone Sodium Phosphate | 0.10-0.12 |
| Edetate Disodium | 0.005-0.02 |
| NaCl | 0.5-0.75 |
| Boric Acid | 0.2-0.4 |
| Benzalkonium Chloride | 0.005-0.015 |
| Tyloxapol | 0.04-0.06 |
| NaOH/HCl | q.s. pH 7.5-8.1 |
| Purified Water | q.s. 100 |

Example 4

Preferred Topical Otic Solution

| Ingredient | Formulation D (% w/v) |
|---|---|
| Moxifloxacin Hydrochloride | $0.545^a$ |
| Dexamethasone Sodium Phosphate | $0.11^b$ |
| Edetate Disodium | $0.01^c$ |
| NaCl | 0.62 |
| Boric Acid | 0.3 |
| Benzalkonium Chloride | 0.01 |
| Tyloxapol | 0.05 |
| $NaOH^d$/HCl | q.s. pH 7.8-8.0 |
| Purified Water | q.s. 100 |

$^a$0.545% is equivalent to 0.5% moxifloxacin as base
$^b$0.11% is equivalent to 0.1% dexamethasone phosphate
$^c$Edetate disodium, dehydrate is used
$^d$Sodium hydroxide equivalent to 0.0972% is added to facilitate dissolution of moxifloxacin hydrochloride. Additional NaOH may be added if required for pH adjustment.

Example 5

Physical stability studies (clarity, precipitates by visual inspection, and pH stability) were conducted for three lots of the composition of Example 4. Samples of the composition were stored in 8 mL opaque LDPE bottles under the following conditions: 4° C./35% relative humidity; 25° C./40% relative humidity; 25° C./40% relative humidity (bottles stored in horizontal position); 30° C./65% relative humidity; 40° C./<25% relative humidity; light cabinet (25° C./40% relative humidity, with an overall illumination of not less than 1.2 million lux hours and integrated near ultraviolet energy of not less than 200 watt-hours/square meter); light cabinet and LDPE bottle in cardboard box; cycling conditions (CY) 1 week with a freeze at −20° C. for 28 hours, then thaw at 30° C. for 28 hours, for a total of 3 cycles in a week. The results are shown in Tables 1-3.

TABLE 1

Clarity

| Storage Condition | Age (Weeks) | Lot 1 | Lot 2 | Lot 3 |
|---|---|---|---|---|
| Initial | 0 | Clear, NMT Ph. Eur. I* | Clear, NMT Ph. Eur. I | Clear, NMT Ph. Eur. I |
| 4° C./35% RH | 52 | Clear, NMT Ph. Eur. I | Clear, NMT Ph. Eur. I | Clear, NMT Ph. Eur. I |
| 25° C./40% RH | 26 | Clear, NMT Ph. Eur. I | Clear, NMT Ph. Eur. I | Clear, NMT Ph. Eur. I |
|  | 52 | Clear, NMT Ph. Eur. I | Clear, NMT Ph. Eur. I | Clear, NMT Ph. Eur. I |
| 25° C./40% RH, Horizontal | 13 | Clear, NMT Ph. Eur. I | Clear, NMT Ph. Eur. I | Clear, NMT Ph. Eur. I |
|  | 26 | Clear, NMT Ph. Eur. I | Clear, NMT Ph. Eur. I | Clear, NMT Ph. Eur. I |
|  | 39 | Clear, NMT Ph. Eur. I | Clear, NMT Ph. Eur. I | Clear, NMT Ph. Eur. I |
|  | 52 | Clear, NMT Ph. Eur. I | Clear, NMT Ph. Eur. I | Clear, NMT Ph. Eur. I |
|  | 78 | Clear, NMT Ph. Eur. I | Clear, NMT Ph. Eur. I | Clear, NMT Ph. Eur. I |
| 30° C./65% RH | 52 | Clear, NMT Ph. Eur. I | Clear, NMT Ph. Eur. I | Clear, NMT Ph. Eur. I |
| 40° C./<25% RH | 13 | Clear, NMT Ph. Eur. I | Clear, NMT Ph. Eur. I | Clear, NMT Ph. Eur. I |
|  | 26 | Clear, NMT Ph. Eur. I | Clear, NMT Ph. Eur. I | Clear, NMT Ph. Eur. I |
| LC | 6 | Clear, NMT Ph. Eur. I | Clear, NMT Ph. Eur. I | Clear, NMT Ph. Eur. I |
| LC/PKG | 6 | Clear, NMT Ph. Eur. I | Clear, NMT Ph. Eur. I | Clear, NMT Ph. Eur. I |
| CY: −20, 30 | 1 | Clear, NMT Ph. Eur. I | Clear, NMT Ph. Eur. I | Clear, NMT Ph. Eur. I |

*"NMT Ph. Eur. I" means that the solution is clearer than European Pharmacopeal clarity standard number I.

TABLE 2

Precipitates

| Storage Condition | Age (Weeks) | Lot 1 | Lot 2 | Lot 3 |
|---|---|---|---|---|
| Initial | 0 | None | None | None |
| 4° C./35% RH | 52 | None | None | None |
| 25° C./40% RH | 26 | None | None | None |
|  | 52 | None | None | None |
| 25° C./40% RH, Horizontal | 13 | None | None | None |
|  | 26 | None | None | None |
|  | 39 | None | None | None |
|  | 52 | None | None | None |
|  | 78 | None | None | None |
| 30° C./65% RH | 52 | None | None | None |
| 40° C./<25% RH | 13 | None | None | None |
|  | 26 | None | None | None |
| LC | 6 | None | None | None |
| LC/PKG | 6 | None | None | None |
| CY: −20, 30 | 1 | None | None | None |

TABLE 3 pH Stability

| Storage Condition | Age (Weeks) | Lot 1 | Lot 2 | Lot 3 |
|---|---|---|---|---|
| Initial | 0 | 7.92 | 7.97 | 7.98 |
| 4° C./35% RH | 52 | 7.89 | 7.89 | 7.90 |
| 25° C./40% RH | 26 | 7.83 | 7.88 | 7.85 |
|  | 52 | 7.89 | 7.89 | 7.90 |
| 25° C./40% RH, Horizontal | 13 | 7.89 | 7.90 | 7.93 |
|  | 26 | 7.83 | 7.89 | 7.86 |
|  | 39 | 7.86 | 7.90 | 7.89 |
|  | 52 | 7.89 | 7.89 | 7.90 |
|  | 78 | 7.87 | 7.90 | 7.92 |
| 30° C./65% RH | 52 | 7.88 | 7.88 | 7.88 |
| 40° C./<25% RH | 13 | 7.89 | 7.91 | 7.94 |
|  | 26 | 7.83 | 7.88 | 7.85 |
| LC | 6 | 7.85, 7.86 | 7.90 | 7.90 |
| LC/PKG | 6 | 7.90 | 7.96 | 7.97 |
| CY: −20, 30 | 1 | 7.92 | 7.91 | 7.91 |

Example 6

The stabilizing effect of various concentrations of tyloxapol in the composition of Example 4 was investigated in a freeze-thaw cycling study. Each cycle consisted of 24 hours at −20° C. followed by 24 hours at room temperature. The compositions were stored in LDPE containers sterilized using ethylene oxide gas or in glass containers. The results are shown in Tables 4 (LDPE containers) and 5 (glass containers).

TABLE 4

(LDPE Containers)

| | | Tyloxapol Concentration | | | | |
|---|---|---|---|---|---|---|
| Cycle | Observations | 0% | 0.02% | 0.03% | 0.04% | 0.05% (Example 4) |
| Initial | Clarity | Clear | Clear | Clear | Clear | Clear |
|  | Color | Yellow | Yellow | Yellow | Yellow | Yellow |
|  | Particles by Visual Observation | No particles | No particles | No particles | No particles | No particles |
|  | pH | 7.909 | 7.926 | 7.917 | 7.915 | 7.910 |

TABLE 4-continued (LDPE Containers)

| | | Tyloxapol Concentration | | | | |
|---|---|---|---|---|---|---|
| Cycle | Observations | 0% | 0.02% | 0.03% | 0.04% | 0.05% (Example 4) |
| Cycle 1 | Clarity | Clear | Clear | Clear | Clear | Clear |
| | Color | Yellow | Yellow | Yellow | Yellow | Yellow |
| | Particles by Visual Observation | No particles | No particles | No particles | No particles | No particles |
| Cycle 2 | Clarity | Clear | Clear | Clear | Clear | Clear |
| | Color | Yellow | Yellow | Yellow | Yellow | Yellow |
| | Particles by Visual Observation | No particles | No particles | No particles | No particles | No particles |
| | pH | 7.886 | 7.900 | 7.882 | 7.897 | 7.893 |
| Cycle 3 | Clarity | Clear | Clear | Clear | Clear | Clear |
| | Color | Yellow | Yellow | Yellow | Yellow | Yellow |
| | Particles by Visual Observation | No particles | No particles | No particles | No particles | No particles |
| Cycle 4 | Clarity | Clear | Clear | Clear | Clear | Clear |
| | Color | Yellow | Yellow | Yellow | Yellow | Yellow |
| | Particles by Visual Observation | 4-5 particles in 4 bottles | 2-3 particles in 4 bottles | No particles | No particles | No particles |
| | pH | 7.877 | 7.893 | 7.918 | 7.903 | 7.906 |

TABLE 5

(Glass Containers)

| | | Tyloxapol Concentration | | | | |
|---|---|---|---|---|---|---|
| Cycle | Observations | 0% | 0.02% | 0.03% | 0.04% | 0.05% (Example 4) |
| Initial | Clarity | Clear | Clear | Clear | Clear | Clear |
| | Color | Yellow | Yellow | Yellow | Yellow | Yellow |
| | Particles by Visual Observation | No particles | No particles | No particles | No particles | No particles |
| | pH | 7.909 | 7.926 | 7.917 | 7.915 | 7.910 |
| Cycle 1 | Clarity | Clear | Clear | Clear | Clear | Clear |
| | Color | Yellow | Yellow | Yellow | Yellow | Yellow |
| | Particles by Visual Observation | No particles | No particles | No particles | No particles | No particles |
| Cycle 2 | Clarity | Clear | Clear | Clear | Clear | Clear |
| | Color | Yellow | Yellow | Yellow | Yellow | Yellow |
| | Particles by Visual Observation | No particles | No particles | No particles | No particles | No particles |
| | pH | 7.885 | 7.911 | 7.909 | 7.908 | 7.910 |
| Cycle 3 | Clarity | Clear | Clear | Clear | Clear | Clear |
| | Color | Yellow | Yellow | Yellow | Yellow | Yellow |
| | Particles by Visual Observation | No particles | No particles | No particles | No particles | No particles |
| Cycle 4 | Clarity | Clear | Clear | Clear | Clear | Clear |
| | Color | Yellow | Yellow | Yellow | Yellow | Yellow |
| | Particles by Visual Observation | 15-20 particles in all bottles | 10-15 particles in all bottles | 9-11 particles in all bottles | 5-10 particles in all bottles | 1-2 particles in all bottles |
| | pH | 7.877 | 7.900 | 7.920 | 7.911 | 7.906 |

Example 7

The physical stability of the indicated moxifloxacin and dexamethasone phosphate solution compositions was tested and the results are shown in Tables 6-9 below.

TABLE 6

Formulations at acidic pH (4.0 to 6.0)

| Component | A | B | C | D | E | F |
|---|---|---|---|---|---|---|
| Moxifloxacin Hydrochloride | 0.545[a] | 0.545[a] | 0.545[a] | 0.545[a] | 0.545[a] | 0.545[a] |
| Dexamethasone Sodium Phosphate | 0.132[b] | 0.132[b] | 0.132[b] | 0.132[b] | 0.132[b] | 0.132[b] |
| Edetate Disodium | 0.01 | 0.01 | 0.01 | 0.01 | 0.01 | 0.01 |
| Boric Acid | 0.3 | 0.3 | 0.3 | 0.3 | 0.3 | 0.3 |
| Citric Acid, Monohydrate | — | — | — | 0.5 | 0.5 | 0.5 |
| Sodium Chloride | 0.62 | 0.5 | 0.5 | — | — | — |
| Glycerin | — | — | — | 1.6 | 1.6 | 1.6 |
| Sorbitol | 0.2 | 0.2 | 0.2 | 0.2 | 0.2 | 0.2 |
| Tyloxapol | 0.05 | 0.05 | 0.05 | 0.05 | 0.05 | 0.05 |
| NaOH/HCl | qs 4.0 ± 0.1 | qs 5.0 ± 0.1 | qs 6.0 ± 0.1 | qs 4.0 ± 0.1 | qs 5.0 ± 0.1 | qs 6.0 ± 0.1 |
| Purified Water | qs 100 | qs 100 | qs 100 | qs 100 | qs 100 | qs 100 |
| Observations | Precipitate[c] | Precipitate[c] | Precipitate[c] | Precipitate | Precipitate | Precipitate |

[a] 0.545% Moxifloxacin hydrochloride is equivalent to 0.5% moxifloxacin as base.
[b] 0.132% Dexamethasone sodium phosphate is equivalent to 0.1% dexamethasone.
[c] The Moxifloxacin did not go into solution until the batch was heated. However as the solution was allowed to cool, crystals began to form in the solution and on the sides of the beaker.

Note:
For Formulations D, E, and F the compounding procedure consisted of two separate parts: part I - Moxifloxacin solution and part II - Dexamethasone Phosphate solution. Both solutions appeared clear. Upon addition of part II to part I, the solutions initially appeared clear but after a few minutes of mixing the solutions became cloudy. Formulation E was brought down to pH 3.5 to see if the solution would become clear, but it did not.

TABLE 7

| Component | G | H | I | J | K | L |
|---|---|---|---|---|---|---|
| Moxifloxacin Hydrochloride | 0.545[a] | 0.545[a] | 0.545[a] | 0.545[a] | 0.545[a] | 0.545[a] |
| Dexamethasone Sodium Phosphate | 0.132[b] | 0.132[b] | 0.132[b] | 0.132[b] | 0.132[b] | 0.132[b] |
| Edetate Disodium | 0.01 | 0.01 | 0.01 | 0.01 | 0.01 | 0.01 |
| Boric Acid | 0.3 | 0.3 | 0.3 | 0.3 | 0.3 | 0.3 |
| Sodium Chloride | 0.44 | 0.44 | 0.36 | 0.36 | 0.26 | 0.19 |
| Mannitol | 0.5 | 0.5 | — | — | — | — |
| Glycerin | — | — | 0.5 | 0.5 | 0.8 | 1.0 |
| Sorbitol | — | — | — | — | — | — |
| Tyloxapol | 0.05 | 0.05 | 0.05 | 0.05 | 0.05 | 0.05 |
| NaOH/HCl | qs 7.2 ± 0.2 | qs 7.3 ± 0.2 | qs 7.2 ± 0.2 | qs 7.3 ± 0.2 | qs 6.8 ± 0.2 | qs 6.8 ± 0.2 |
| Purified Water | qs 100 | qs 100 | qs 100 | qs 100 | qs 100 | qs 100 |
| Observations - Day 1 @ 5° C. | Precipitate | Precipitate | Precipitate | Clear | Precipitate[d] | Precipitate[d] |
| Observations - Day 6 @ RT | Precipitate | Precipitate | Precipitate | Precipitate[c] | NA | NA |
| Observations - Day 12 @ RT | Precipitate | Precipitate | Precipitate | Precipitate | NA | NA |
| Observations - Day 14 @ RT | Precipitate | Precipitate | Precipitate | Precipitate | NA | NA |

[a] 0.545% Moxifloxacin hydrochloride is equivalent to 0.5% moxifloxacin as base.
[b] 0.132% Dexamethasone sodium phosphate is equivalent to 0.1% dexamethasone.
[c] This sample was stored at 5° C. and observed to have precipitate upon removal from 5° C. The sample was allowed to sit at RT but precipitate was still observed.
[d] Precipitate was observed as soon as compounding was completed.

TABLE 8

| Component | M[c] | N[c] | O | P | Q | R[c] | S[c] | T | U | V |
|---|---|---|---|---|---|---|---|---|---|---|
| Moxifloxacin Hydrochloride | 0.545[a] | 0.545[a] | 0.545[a] | 0.545[a] | 0.545[a] | 0.545[a] | 0.545[a] | 0.545[a] | 0.545[a] | 0.545[a] |
| Dexamethasone Sodium Phosphate | 0.132[b] | 0.132[b] | 0.132[b] | 0.132[b] | 0.132[b] | 0.132[b] | 0.132[b] | 0.132[b] | 0.132[b] | 0.132[b] |
| Edetate Disodium | 0.01 | 0.01 | 0.01 | 0.01 | 0.01 | 0.01 | 0.01 | 0.01 | 0.01 | 0.01 |
| Boric Acid | 0.01 | 0.01 | 0.01 | 0.01 | 0.01 | 0.03 | 0.03 | 0.03 | 0.03 | 0.03 |
| Sodium Borate | 0.44 | 0.44 | 0.44 | 0.44 | 0.44 | 0.42 | 0.42 | 0.42 | 0.42 | 0.42 |
| Sodium Citrate | — | — | — | — | — | 1.0 | 1.0 | 1.0 | 1.0 | 1.0 |
| Sodium Chloride | 0.5 | 0.5 | 0.5 | 0.5 | 0.5 | 0.27 | 0.27 | 0.27 | 0.27 | 0.27 |
| Sorbitol | 0.2 | 0.2 | 0.2 | 0.2 | 0.2 | 0.2 | 0.2 | 0.2 | 0.2 | 0.2 |

TABLE 8-continued

| Component | M[C] | N[C] | O | P | Q | R[C] | S[C] | T | U | V |
|---|---|---|---|---|---|---|---|---|---|---|
| Tyloxapol | 0.05 | 0.05 | 0.05 | 0.05 | 0.05 | 0.05 | 0.05 | 0.05 | 0.05 | 0.05 |
| NaOH/HCl | qs 6.8 ± 0.2 | qs 7.0 ± 0.2 | qs 7.1 ± 0.2 | qs 7.2 ± 0.2 | qs 7.3 ± 0.2 | qs 6.8 ± 0.2 | qs 7.0 ± 0.2 | qs 7.1 ± 0.2 | qs 7.2 ± 0.2 | qs 7.3 ± 0.2 |
| Purified Water | qs 100 | qs 100 | qs 100 | qs 100 | qs 100 | qs 100 | qs 100 | qs 100 | qs 100 | qs 100 |
| Day 4 Observations | NA | NA | Precipitate | Precipitate | Clear | NA | NA | Precipitate | Precipitate | Clear |
| Day 11 Observations | NA | NA | NA | NA | 1 of 2 Precipitate | NA | NA | NA | NA | Clear |
| Day 18 Observations | NA | NA | NA | NA | Both Precipitate | NA | NA | NA | NA | Clear |
| Day 25 Observations | NA | NA | NA | NA | NA | NA | NA | NA | NA | Clear |
| Day 32 Observations | NA | NA | NA | NA | NA | NA | NA | NA | NA | Precipitate |

[a]0.545% Moxifloxacin hydrochloride is equivalent to 0.5% moxifloxacin as base.
[b]0.132% Dexamethasone sodium phosphate is equivalent to 0.1% dexamethasone.
[c]These formulations were discarded due to precipitate formation at completion of the compounding process.

TABLE 9

| Component | W | X | Y | Z | AA | AB | AC | AD | AE | AF |
|---|---|---|---|---|---|---|---|---|---|---|
| Moxifloxacin Hydrochloride | 0.545[a] | 0.545[a] | 0.545[a] | 0.545[a] | 0.545[a] | 0.545[a] | 0.545[a] | 0.545[a] | 0.545[a] | 0.545[a] |
| Dexamethasone Sodium Phosphate | 0.132[b] | 0.132[b] | 0.132[b] | 0.132[b] | 0.132[b] | 0.132[b] | 0.132[b] | 0.132[b] | 0.132[b] | 0.132[b] |
| Edetate Disodium | 0.01 | 0.01 | 0.01 | 0.01 | 0.01 | 0.01 | 0.01 | 0.01 | 0.01 | 0.01 |
| Boric Acid | 0.3 | 0.3 | 0.3 | 0.3 | 0.3 | 0.3 | 0.3 | 0.3 | 0.3 | 0.3 |
| Sodium Chloride | 0.5 | 0.5 | 0.5 | 0.5 | 0.5 | — | — | — | — | — |
| Sorbitol | 0.2 | 0.2 | 0.2 | 0.2 | 0.2 | 0.2 | 0.2 | 0.2 | 0.2 | 0.2 |
| Tyloxapol | 0.05 | 0.05 | 0.05 | 0.05 | 0.05 | 0.05 | 0.05 | 0.05 | 0.05 | 0.05 |
| NaOH/HCl | qs 7.0 ± 0.2 | qs 7.3 ± 0.2 | qs 7.4 ± 0.2 | qs 7.8 ± 0.2 | qs 7.2 ± 0.2 | qs 7.0 ± 0.2 | qs 7.2 ± 0.2 | qs 7.3 ± 0.2 | qs 7.4 ± 0.2 | qs 7.8 ± 0.2 |
| Purified Water | qs 100 | qs 100 | qs 100 | qs 100 | qs 100 | qs 100 | qs 100 | qs 100 | qs 100 | qs 100 |
| Day 10 Observations | Precipitate | Clear | Clear | Clear | Precipitate | Precipitate | Precipitate | Precipitate | Precipitate | Clear |
| Day 17 Observations | NA | Precipitate | Clear | Clear | NA | NA | NA | NA | NA | Clear |
| Day 24 Observations | NA | NA | Clear | Clear | NA | NA | NA | NA | NA | Precipitate |
| Day 31 Observations | NA | NA | Clear | Clear | NA | NA | NA | NA | NA | NA |
| Day 38 Observations | NA | NA | Clear | Clear | NA | NA | NA | NA | NA | NA |
| Day 45 Observations | NA | NA | Clear | Clear | NA | NA | NA | NA | NA | NA |
| 18-week Observations | NA | NA | Clear | Clear | NA | NA | NA | NA | NA | NA |
| 24-week Observations | NA | NA | Some Precipitate | Clear | NA | NA | NA | NA | NA | NA |
| 28-week Observations | NA | NA | More Precipitate | Clear | NA | NA | NA | NA | NA | NA |

[a]0.545% Moxifloxacin hydrochloride is equivalent to 0.5% moxifloxacin as base.
[b]0.132% Dexamethasone sodium phosphate is equivalent to 0.1% dexamethasone.

Example 10

The composition of Example 2 was subjected to preservative efficacy testing. Antimicrobial preservative effectiveness was determined using an organism challenge test according to the methods described in the United States Pharmacopeia (USP) and European Pharmacopoeia (Ph.Eur.). Samples were inoculated with known levels of one or more of the following: gram-positive (Staphylococcus aureus ATCC 6538) and gram-negative (Pseudomonas aeruginosa ATCC 9027 and Escherichia coli ATCC 8739) vegetative bacteria, yeast (Candida albicans ATCC 10231) and mold (Aspergillus niger ATCC 16404). The samples were then pulled at specified intervals to determine if the antimicrobial preservative system was capable of killing or inhibiting the propagation of organisms purposely introduced into the formulation. The rate or level of antimicrobial activity determines compliance with the USP and/or Ph.Eur. preservative efficacy standards for ophthalmic preparations.

The compendial preservative standards for ophthalmic preparations are presented below:

For Bacteria:

| | Log Reduction of Organism Population | | |
|---|---|---|---|
| Time Pull | USP | Ph. Eur. A | Ph. Eur. B (Min) |
| 6 hours | — | 2 | — |
| 24 hours | — | 3 | 1 |
| 7 days | — | — | 3 |
| 14 days | 3 | — | — |
| 28 days | NI | NR | NI |

For Fungi:

| Time Pull | USP | Ph. Eur. A | Ph. Eur. B (Min) |
|---|---|---|---|
| 7 days | — | 2 | — |
| 14 days | NI | — | 1 |
| 28 days | NI | NI | NI |

NR = No organisms recovered
NI = No increase at this or any following time pulls
— = No requirement at this time pull The results of the microorganism challenge test are shown in Table 10 below.

TABLE 10

| Composition | USP | Ph. Eur. B | Ph. Eur. A |
|---|---|---|---|
| Example 2 | Pass | Pass | Fail |

Example 11

The composition of Example 4 was subjected to the same preservative efficacy testing described in Example 10. Additionally, similar compositions containing varying concentrations of benzalkonium chloride were tested. The compositions and the preservative efficacy testing results are shown in Table 11.

TABLE 11

| Components | AG | AH | AI | AJ | Example 4 |
|---|---|---|---|---|---|
| Moxifloxacin Hydrochloride, NOC | $0.545^a$ | $0.545^a$ | $0.545^a$ | $0.545^a$ | $0.545^a$ |
| Dexamethasone Sodium Phosphate, USP | $0.11^b$ | $0.11^b$ | $0.11^b$ | $0.11^b$ | $0.11^b$ |
| Benzalkonium Chloride, NF | 0.0 | 0.0025 | 0.005 | 0.0075 | 0.01 |
| Edetate Disodium, USP | 0.01 | 0.01 | 0.01 | 0.01 | 0.01 |
| Boric Acid, NF | 0.3 | 0.3 | 0.3 | 0.3 | 0.3 |
| Sodium Chloride, USP | 0.62 | 0.62 | 0.62 | 0.62 | 0.62 |
| Tyloxapol, USP | 0.05 | 0.05 | 0.05 | 0.05 | 0.05 |
| Sodium Hydroxide, NF and/or Hydrochloric Acid, NF | Adjust pH to 7.9 ± 0.1 | Adjust pH to 7.9 ± 0.1 | Adjust pH to 7.9 ± 0.1 | Adjust pH to 7.9 ± 0.1 | Adjust pH to 7.9 ± 0.1 |
| Purified Water, USP | qs 100 | qs 100 | qs 100 | qs 100 | qs 100 |
| Preservative Effectiveness Test (PET) Results | Pass USP/EPB Fail EPA | Pass USP/EPB Fail EPA | Pass USP/EPB Fail EPA | Pass USP/EPB/EPA | Pass USP/EPB/EPA |

$^a$0.545% Moxifloxacin hydrochloride is equivalent to 0.5% moxifloxacin as base.
$^b$0.11% Dexamethasone sodium phosphate is equivalent to 0.1%, dexamethasone phosphate.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating an otic infection comprising topically administering to the ear a solution composition consisting essentially of
   a) 0.545% (w/v) moxifloxacin hydrochloride;
   b) 0.11% (w/v) dexamethasone sodium phosphate;
   c) 0.01% (w/v) edetate disodium;
   d) 0.5-0.75% (w/v) sodium chloride;
   e) 0.3% (w/v) boric acid;
   f) 0.01% (w/v) benzalkonium chloride;
   g) 0.05% (w/v) tyloxapol;
   h) NaOH or HCl in an amount sufficient to cause the composition to have a pH from 7.8-8.0; and
   i) water.

* * * * *